United States Patent [19]

Melgaard

[11] Patent Number: 4,988,288
[45] Date of Patent: Jan. 29, 1991

[54] MATERIAL HEATING OVEN

[75] Inventor: Hans L. Melgaard, Minneapolis, Minn.

[73] Assignee: Despatch Industries, Inc., Minneapolis, Minn.

[21] Appl. No.: 398,229

[22] Filed: Aug. 21, 1989

Related U.S. Application Data

[63] Continuation of Ser. No. 193,876, May 13, 1988, abandoned.

[51] Int. Cl.$^5$ .................................................. F27B 9/04
[52] U.S. Cl. ..................................... 432/72; 432/152
[58] Field of Search ................... 432/8, 59, 72, 144, 432/152

[56] References Cited

U.S. PATENT DOCUMENTS

| | | | |
|---|---|---|---|
| 2,222,809 | 11/1940 | Curran | 432/152 |
| 2,750,680 | 6/1956 | Houdry et al. | 432/72 |
| 3,186,698 | 6/1965 | Thome | 432/152 |
| 3,437,422 | 4/1969 | Guckel . | |
| 3,581,679 | 6/1971 | Jansen | 432/152 |
| 3,899,862 | 8/1973 | Muys et al. . | |
| 3,977,091 | 8/1976 | Hortig et al. . | |
| 4,140,479 | 2/1979 | Sirch et al. | 432/152 |
| 4,321,031 | 3/1982 | Woodgate | 432/152 |
| 4,349,508 | 9/1982 | Liede . | |
| 4,597,192 | 7/1986 | Sfondrini et al. . | |

Primary Examiner—Henry C. Yuen
Attorney, Agent, or Firm—James R. Haller; Mary P. Bauman; Gregory P. Kaihoi

[57] ABSTRACT

A material heating oven for sterilizing items for use in a sterile environment or the like comprising a hot air supply device having a filter, a cool air supply device having a filter, an oven cavity separate from the hot air supply and cool air supply devices, and a dampering system for selectively drawing air from the hot air supply and cool air supply devices to regulate the temperature of the oven cavity. Both the hot air supply and cool air supply devices include independent air recirculation loops for maintaining substantially constant temperature airstreams from which selected quantities of air are exchanged with the oven cavity. The nearly constant temperature airstreams prevent the filters in the devices from being thermally stressed which may cause them to shed particles to the clean environment. An electrically controlled temperature control system is used to regulate the temperature of the airstream flowing through the hot air supply and cool air supply devices.

6 Claims, 1 Drawing Sheet

MATERIAL HEATING OVEN

This application is a continuation of application Ser. No. 193,876, filed May 13, 1988, now abandoned.

FIELD OF THE INVENTION

The invention relates to material heating equipment and, more particularly to an oven for depyrogenating, batch drying and critical finish drying items for use in clean rooms, manufacturing areas, and other sterile environments.

BACKGROUND OF THE INVENTION

Depyrogenation is a cleaning process in which fever-causing bacterial carcasses, or other materials, pyrogens, are oxidized to remove them from the surfaces of objects such as glassware. Depyrogenation is commonly performed on materials prior to their introduction to an environment having a precisely controlled particle density such as a clean room, a laboratory, or a production area.

In order to depyrogenate many objects, the objects are heated to approximately 230°-270° C. in a clean room environment, i.e., an environment having a precisely controlled particle density in its atmosphere. Desired particle densities may be obtained by passing air through specialized filters (e.g., HEPA filters) of various sizes to filter out particulate matter above given size ranges. However, if air travelling through a filter changes in temperature at a rate of about 2° C. per minute or more, the resulting thermal shock or stressing of the filter may cause the filter itself to emit particulate matter into the air. The quantity of particulate matter emitted varies with the rate of temperature change of the air provided to the filter.

In the past, it has generally been necessary to heat the air supplied to a depyrogenation oven at a rate of not greater than about 2° C. per minute to avoid thermal stress to in-line filters. A heating rate of less than 2° C. per minute can require a heating time of approximately two hours to reach a suitable depyrogenation temperature. Long heating and cooling times substantially reduce the output of a depyrogenation oven.

It would be desirable to provide a depyrogenation oven that can be heated quickly with filtered air to a desired depyrogenation operating temperature without causing emission of particulate material from a filter due to thermal stress.

SUMMARY OF THE INVENTION

The invention relates to a material heating oven having an oven cavity. Hot air supply means separate from the oven cavity is provided, comprising air heating means, blower means and air filter means. Conduit means are provided for continuously recirculating air through the air heating means and filter means and for supplying heated air to the filter means at substantially a constant, controlled temperature, the conduit means defining a recirculation loop. Duct means are provided to communicate the conduit means with the oven cavity to deliver heated, filtered air to the cavity. Control means is provided to selectively control the temperature and volumetric flow rate of air drawn from the air heating means to heat the oven cavity. Because the air supplied to the filter remains at a substantially constant temperature, thermal stressing of the filter may be avoided while yet permitting the oven cavity to be rapidly heated. In the recirculation loop heated, filtered air is withdrawn through the duct means immediately downstream from the filter and is directed to the oven cavity. Air from the oven cavity may be recirculated by means of a return duct to the recirculation loop, such return air being delivered to the loop upstream from the heating means.

A separate cooling means may also be provided to supply filtered, cooler air to the oven cavity to cool down the depyrolized objects. The cooling means are separate from the oven cavity and may comprise a cooling element, a blower, a filter, and conduit means defining, with the cooling element, blower and filter, a recirculative loop for recirculating cooled air through the filter at substantially a constant, controlled temperature. Second duct means are provided to communicate the recirculative loop of the air cooling means at a point downstream of the filter means with the oven cavity to deliver cool, filtered air to the cavity, and control means are provided to control the temperature of air supplied to the filter. The cooling means desirably also includes a heater for heating air that is recirculated through the loop for the purpose of depyrolyzing and sterilizing the loop, particles emitted from the filter due to rapid heating and cooling thereof being in turn removed by the filter from the recirculating air stream.

In a preferred embodiment, the oven cavity is elongated and is provided with means for transporting objects through the cavity. In this embodiment, heated, filtered air is initially supplied to the objects to heat them, and as the objects move through the oven cavity, cooler, filtered air is provided to cool the objects. Objects to be depyrolyzed move from a relatively dirty, particle laden environment adjacent one end of the oven cavity to a relatively clean, controlled particle density environment adjacent the other end of the oven cavity. The clean environment is maintained at a pressure such that any air flow between the oven cavity and the clean environment is in a direction from the clean environment into the oven cavity. Similarly, the air pressure within the oven cavity is maintained such that movement of air between it and the comparatively dirty or particle laden environment is toward the latter environment.

DETAILED DESCRIPTION OF THE PREFERRED EMBODIMENTS

Figure 1:
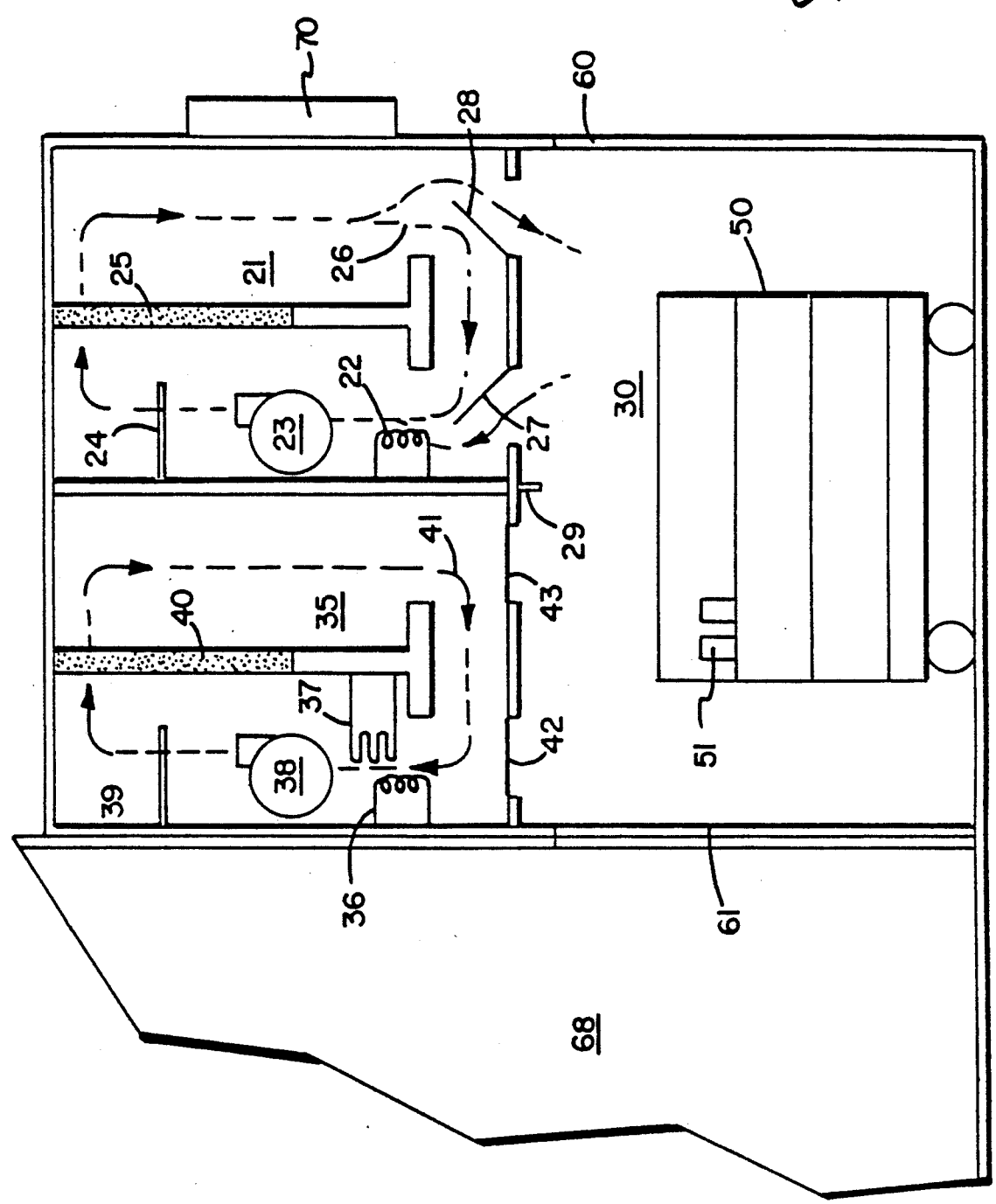
FIG. 1 is a schematic elevational view of a batch depyrogenation oven of the invention with the side portion removed to show interior detail.

The invention comprises a material heating system employing a temperature control system capable of heating an oven cavity quickly and cleanly to an elevated temperature for processes such as depyrogenation.

With reference to FIG. 1, a hot air supply means is shown generally as 21 and, in operation, maintains air circulating therein at an elevated temperature, typically approximately 260° C. A cool air supply is shown generally at 35 and, in operation, maintains air circulating therein at a lower temperature, typically in the range of 20°-50° C. When incorporated in a batch material heating system, as exemplified in FIG. 1, the hot air supply 21 and the cool air supply 35 are operatively connected to the oven cavity 30 by means of ductwork including a PID (proportional integral and derivative) electronically controlled damper system to control the flow of heated or unheated air to the oven cavity 30 to regulate its temperature.

The hot air supply 21 includes walls defining an air recirculating loop shown in phantom lines at 26. The air supply 21 includes an air heating element 22, shown schematically as an electric resistance heater in the recirculation loop and across which air is channeled for heating. Air is driven through the recirculation loop 26 by a blower such as an electric fan 23, and a filter 25, positioned within the loop and downstream from the heating element 22, filters particles above a predetermined size from the air stream. A temperature control sensor 24 is positioned upstream of the filter 25 to sense the temperature of air supplied to the filter.

In operation, air is drawn from the oven cavity 30 or from elsewhere into the hot air supply 21 through an inlet damper 27, the latter being selectively controlled by an electronic controller 70 in response to a signal received from the temperature sensor 24. The air stream is heated by the heating element 22 and passes through the filter 25, following which all or a portion of it is channeled back to the oven cavity 30 through an outlet damper 28 or into the recirculation loop 26 whereby it is returned to the heating element 22. At certain times when hot air is not demanded by the oven cavity 30, the hot air stream is wholly recirculated past the heating element 22 and through the filter 25 in the separate recirculation loop 26.

Initially, air circulating in the recirculation loop 26 of the hot air supply 21 may be heated rapidly by the heating element 22 to depyrogenation temperatures because any particles emitted by the filter 25 through thermal stress are in turn recaptured by the filter 25 and are removed from the air stream. However, once the damper doors 27,28 are opened to allow air to bleed into and circulate through the oven cavity 30, the temperature of the air is controlled to avoid thermally stressing the filter 25. This may be accomplished by controlling the relative volumetric flow rates of recirculated air and air supplied to the oven cavity (by controlling, e.g., the dampers), or by controlling the power supplied to the heating element 22, or both, such control being provided by the controller 70 in response to temperature sensed by the sensor 24. The controller 70 also monitors the temperature of the oven cavity 30 by means of a temperature sensor 29.

The cool air supply device 35 cools the air in the oven cavity 30 as is desired. The device is similar to the hot air supply 21 in that it comprises a heating element 36, a fan 38, a temperature sensor 39, a filter 40, and inlet and outlet dampers 42 and 43, respectively. However, the cool air supply 35 further includes a cooling coil 37 through which a coolant may flow to cool the air flowing through the device. Air recirculating in the cool air supply device 35 is maintained at a substantially constant operating temperature in the range of about 20°-50° C. The dampers 42, 43 on the cool air supply device 35 are controlled by the electronic controller 70 or a separate, similar controller which regulates the volume flow rate of air exchanged between the oven cavity 30 and the device 35. As shown in FIG. 1, the cool air supply device 35 has a recirculation loop, shown in phantom lines as 41, enabling cool filtered air to recirculate through the cooling coil 37 and through the filter 40.

In order to rapidly sterilize the cool air supply device 35 so that it may supply clean, filtered, cool air to the oven cavity, the dampers 42,43 are placed in a closed position and liquid coolant is drained from the cooling coils 37. The heating element 36 is then activated and the device is heated to a suitable depyrogenation temperature. The temperature can be raised at a rate greatly exceeding 2° C. per minute because the device is in a recirculation mode disconnected from the oven cavity 30 and any particles emitted from the filter 40 will be recaptured by the filter 40 on their next pass through the device. After the air cooling device 35 has been maintained at an elevated temperature for a time sufficient to sterilize and depyrogenate itself, the heating element 36 is deactivated, the cooling coil 37 is charged with coolant, and the device is cooled to a temperature of approximately 50° C. After the device 35 has been depyrogenated, it is ready to be used to control the temperature of the cavity 30. The cool air supply device 35 will remain depyrogenated while the device is in operation and will not have to be re-depyrogenated until it is turned off or exposed to a dirty environment.

Initial depyrogenation is required for the cool air supply device 35 because the temperature at which it is maintained may support the growth of bacteria and other microorganisms. The cool air supply device 35 desirably is operated in the temperature range of about 20° C. to about 50° C.

The hot and cool air supply devices 21,35 are desirably used alternately to control the temperature of the oven cavity 30 to which they supply air as batches of objects are loaded onto and are removed from the oven cavity. The temperature of the oven cavity 30 is regulated by selectively varying the power supplied to the heater 22 carried by the hot air supply 21 and by regulating the dampers 27,28. The controller 70 selectively controls the operation of the dampering system and the hot air supply and cool air supply devices 21,35 in response to input from the temperature sensors 24,29,39 carried by the supply devices 21,35 and the oven cavity 30, respectively. The dampers may be selectively opened and closed to regulate the amount of air exchanged between the oven cavity 30 and the supply devices. In a preferred embodiment, a PID controller is included for maintaining a pressure differential between the sterile environment 68, the environment of the oven cavity 30, and the room environment 69. A plurality of pressure transducers may be carried by the aforementioned environments and operatively connected to the controller to detect and control the pressures of those environments. The PID controller includes computing means for computing the pressure differentials between adjacent environments. The system preferably further includes pressure control means such as a variable speed blower and an exhaust channel, operatively contained within selected environments.

It is desirable to maintain the sterile environment 68 at a greater positive pressure than other adjacent environments to prevent contamination. It is also desirable to maintain the oven cavity 30 at a greater positive pressure than the room environment 69 to maintain flow of air, if any, in a direction from the cleaner environment (e.g., the oven cavity) to the dirtier environment (e.g., the room environment 69) to prevent contamination. A preferred pressure state for the system is one in which the oven cavity 30 is maintained at a positive pressure that is approximately the average of the pressures contained by the sterile environment 68 and the room environment 69.

To begin operating the material heating oven of the invention, heat transfer fluid is drained from the cooling coil 37 and the hot and cool air supplies 21,35 are heated rapidly to suitable depyrogenation temperatures. After a time period sufficient to sterilize and depyrogenate the cool air supply device 35, the cool air supply is cooled to approximately 50° C. and cooling coil 37 is filled with coolant. A cart 50 containing items to be sterilized such as glassware 51 is introduced into the oven cavity 30 through door 60, door 61 remaining closed. Door 60 is closed, and when the oven cavity 30 is ready to be heated, the input damper 27 is slowly opened to allow air to enter the hot air supply 21 from the oven cavity 30. Simultaneously, the outlet damper 28 is slowly opened to permit heated air from the circulating air stream 26 to enter the oven cavity 30. The air entering the hot air supply device 21 is heated by the heating coil 22 and then transported past the temperature sensor 24 which is carried immediately upstream of the filter 25. If the sensed air temperature sampled by the sensor 24 is changing at a rate likely to cause the filter to emit particles (e.g., a rate approaching 2° C. per minute), the control system 70 responds by increasing the power supplied to the heating coil 22 to reduce the rate of change to an acceptable level (e.g., less than 2° C. per minute). The air in the oven cavity 30 is heated in this manner until a desired temperature (generally at least 230° C.) is attained for sterilization and depyrogenation of the contents of the oven cavity 30. The oven cavity 30 is preferably maintained at this temperature for a time period enabling full depyrogenation to occur. After depyrogenation has been completed, the dampers 27,28 connecting the hot air supply device 21 to the oven cavity 30 are closed.

To cool the oven cavity 30, air is exchanged in a similar manner between the cool air supply device 35 and the oven cavity 30. The dampers 42,43 connecting the air cooling device 35 to the oven cavity 30 are slowly opened to let some cool air into the oven cavity and to allow some hot air from the oven cavity 30 enter the air supply device 35. The latter air stream is cooled by the cooling coil 37 and channeled past a temperature sensor 39 carried upstream of the filter 40. The rate of temperature change is sensed and the temperature of the heat transfer fluid supplied to the cooling coil 37 is selectively controlled to keep the rate within predetermined allowable limits. The oven cavity 30 is cooled in this manner until it reaches a desired temperature at which time the damper doors 42,43 are closed. When the glassware 51 and other items reach an acceptable temperature, the door 61 connecting the oven cavity 30 to the sterile environment 68 is opened and the cart 50 is transferred into the sterile environment.

In this configuration, the oven cavity 30 may be heated rapidly without concern for filter stress because the oven cavity 30 does not contain a filter. Air may be transferred rapidly to the oven cavity 30 as long as the air streams within the air supply devices 21,35 remain within their respective allowable temperature change limits. An important use of the system is to rapidly depyrogenate glassware and other materials for use in a clean room environment. The air heating and cooling devices 21 and 35 are used to rapidly change the temperature of the oven cavity 30 while maintaining the rate of temperature change of air flowing through the filters within certain specified limits. Limiting the rate of air temperature change of the air supplied to the filters reduces the risk of the filters shedding particles through thermal stress.

The material heating oven described above is employed in batch process depyrogenation. Carts 50 containing objects to be depyrogenated may be loaded into the oven cavity 30 through a set of electronically-operated interlocking doors 60. The objects are depyrogenated and cooled according to the process described above and are removed through another set of interlocking doors 61 connecting the oven cavity 30 to the sterile environment 68. The room environment 69 in which the cart is contained prior to loading into the oven cavity 30 may be relatively "dirty" containing, for example, approximately 10,000 particles/ft.$^3$. The oven desirably removes a sufficient number of particles to enable the cart and contents to be acceptable to a sterile environment which is approximately a Class 10 or a Class 100 environment (containing 10 to 100 particles per ft.$^3$, respectively).

The present invention has several important advantages over previous systems. The system enables objects in an oven cavity to be heated much more quickly than is permitted by a 2° C. per minute temperature rise. The unique configuration of the system allows the oven cavity 30 to be heated and cooled rapidly while the rate of temperature change of the air flowing through the air supply devices is precisely controlled to prevent thermal filter stressing.

While a preferred embodiment of the present invention has been described, it should be understood that various changes, adaptations and modifications may be made therein without departing from the spirit of the invention and the scope of the appended claims.

What is claimed is:

1. A material heating oven comprising an oven cavity, hot air supply means separate from the oven cavity and comprising heating means for heating air passing therethrough, a blower, a filter, and conduit means defining, with the heating means, blower and filter, an air recycling loop for recirculating air through the heater and filter at a substantially constant, controlled temperature; first controllable duct means for communicating the conduit means of the hot air supply means with the oven cavity to deliver heated, filtered air to the cavity at a controlled flow rate; first control means for controlling the temperature of the air supply to the filter of the hot air supply means; cool air supply means separate from the oven cavity and comprising a cooling element, a blower, a filter, and conduit means defining, with the cooling element, blower and filter, an air recycling loop for recirculating air through the cooling element and filter at a substantially constant, controlled temperature; second controllable duct means for communicating the conduit means of the cool air supply means with the oven cavity to deliver cooled, filtered air to the cavity; second control means for controlling the temperature of the air supply to the filter of the cool air supply means; said first and second controllable duct means including electronic control means for controlling the volumetric flow rate of air supply to the oven cavity from the hot air supply means and cool air supply means.

2. The material heating oven of claim 1 wherein the air cooling means includes a heater for supplying heated air to the air recycling loop to sterilize and depyrogenate the air recycling loop.

3. The material heating oven of claim 1, wherein the oven cavity comprises an insulated enclosure having doors at opposite ends thereof, and interlocking means preventing the doors from being opened simultaneously, one door being carried adjacent a first environment having a controlled particle density and the other door being carried adjacent a second environment having a higher particle density.

4. The material heating oven of claim 3 including means for providing a pressure differential between the oven cavity and the first and second environments, the first environment being maintained at a greater positive pressure than the oven cavity, and the oven cavity being maintained at a greater positive pressure than the second environment so that any air exchanged between the environments flows toward the environment having a higher particle density.

5. The material heating oven of claim 1 wherein the electronic control means includes a plurality of temperature sensors for sensing the temperature of the air streams within the hot air supply, the cool air supply and the oven cavity, for controlling the operating temperatures of the same in response to the temperatures detected by the temperature sensors.

6. A material heating oven comprising an oven cavity, hot air supply means separate from the oven cavity and comprising heating means for heating air passing therethrough, a blower, a filter, conduit means for continuously recirculating air through the heater and filter and for supplying air to the controlled duct means for communicating the conduit means with the oven cavity to deliver heated, filtered air to the cavity at a controlled flow rate, and control means for controlling the temperature of the air supply to the filter, air cooling means separate from the oven cavity and comprising a cooling element, a blower, a filter, and conduit means defining, with the cooling element, blower and filter, an air recycling loop for recirculating air through the cooling element and filter at substantially a constant, controlled temperature, second controlled duct means for communicating the conduit means with the oven cavity to deliver cooled, filtered air to the cavity, and control means for controlling the temperature of the air supply to the filter, the air cooling means including a heater for supplying heated air to the air recycling loop to sterilze and depyrogenate the air recycling loop, the control duct means including an electronic control means for controlling the volumetric flow rate of air supplied to the oven cavity from the hot air supply and cool air supply means, the oven cavity including interlocking door means preventing the doors from being opened simultaneously, one door being carried adjacent a first environment having a controlled particle density and the other door being carried adjacent a second environment having a higher particle density, means for providing a pressure differential between the oven cavity and the first and second environments, the first environment being maintained at a greater positive pressure than the oven cavity, and the oven cavity being maintained at a greater positive pressure than the second environment so that any air exchanged between the environments flows in the direction of the environment having a higher particle density, the electronic control means including a plurality of temperature sensors for sensing the temperature of the air streams within the hot air supply, the cool air supply and the oven cavity, for controlling the operating temperatures of the same in response to the temperatures detected by the temperature sensors.

* * * * *